US00PP28925P3

(12) United States Plant Patent
Salman

(10) Patent No.: US PP28,925 P3
(45) Date of Patent: Jan. 30, 2018

(54) *SALVIA* PLANT NAMED 'LITTLE NIGHT'

(50) Latin Name: ***Salvia nemerosa* (superba)**
Varietal Denomination: Little Night

(71) Applicant: David Mark Salman, Santa Fe, NM (US)

(72) Inventor: David Mark Salman, Santa Fe, NM (US)

(73) Assignee: Waterwise Gardening, LLC, Santa Fe, NM (US)

( * ) Notice: Subject to any disclaimer, the term of this patent is extended or adjusted under 35 U.S.C. 154(b) by 0 days.

(21) Appl. No.: 14/757,117

(22) Filed: Nov. 20, 2015

(65) Prior Publication Data

US 2017/0150673 P1 May 25, 2017

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

PUBLICATIONS

The National Gardening Association Plants Database "*Salvia*", retrieved from Internet on Jan. 26, 2017. (4 pages total).*
Highcountrygardens.com, "*Salvia sylvestris* Little Night PPAF Little Night European Sage—2015 Plant of the Year", Retrieved at <<https://www.highcountrygardens.com/salvia-sylvestris-little-night>> on Aug. 10, 2017, Published Nov. 21, 2014. 8 pages.
High Country Gardens, "Spring 2015 Catalog and Plants of the Year", Distributed Jan. 12, 2015, 4 pages.

* cited by examiner

*Primary Examiner* — Susan McCormick Ewoldt

(57) ABSTRACT

A new and distinct variety of European Meadow Sage named 'Little Night' that is characterized by its dwarf, compact habit and dark violet-blue flowers. Additionally, the flowering stems (spikes) are short and compact with small-sized foliage.

2 Drawing Sheets

Figure 1:
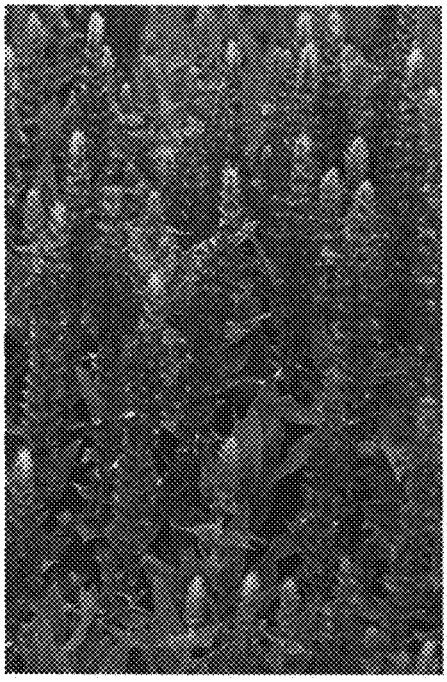

Latin name of the genus and species of the plant claimed: The ornamental plant variety of this invention is botanically identified as *Salvia nemerosa* (superba).

Variety denomination: The variety denomination is 'Little Night'.

BACKGROUND OF THE INVENTION

The present invention relates to a new and distinct plant variety of *Salvia nemerosa* (superba), more commonly known as European Meadow Sage. The new variety has dwarf-like characteristics, including: compact growth habit; short, compact flowering stems (spikes); and small-sized foliage.

European Meadow Sage is a perennial, ornamental plant used in garden landscapes. Its attractive violet-blue flowers and adaptation to a variety of soil conditions, including clay, contribute to its broad market appeal and utilization.

Discovered and asexually propagated by the inventor, 'Little Night' was selected from a cultivated area in a residential garden located in Salt Lake City, Utah on Jun. 8, 2011. While the exact parentage of the present invention is uncertain, 'Little Night' is likely an un-hybridized garden seedling of *Salvia nemerosa* (superba) 'May Night'. This statement is based on the observation of the surrounding plants where the invention was discovered in that 'May Night' was the only species of *salvia* plants in the area. 'Little Night' distinguished itself from the surrounding seedlings through its much smaller mature-sized stems and the shorter length of flower spikes.

In July 2011, the discovered invention was transported and replanted into a pot and cultivated in a greenhouse located in Santa Fe, N.Mex. where it was observed for two years. Also, propagation via vegetative cuttings of the originally transported plant began in August of 2011 under the direction of the inventor of the present invention. The method utilized softwood cuttings dipped in a standard-strength rooting hormone. The cuttings were then placed under intermittent mist for approximately 4 weeks until they rooted. Propagation testing continued at the greenhouse located in Santa Fe, N.Mex. of the rooted cuttings for two generations. These cuttings maintained the small size, flower color and other characteristics of the discovered invention. Additional cuttings were taken from 2nd generation plants grown from cuttings of the discovered invention, which also maintained the small size, flower color and other characteristics of the discovered invention. This testing demonstrated that the distinct characteristics described herein are true-to-type and transmissible by asexual reproduction with uniformity and stability. These results were confirmed via additional testing in Landenberg, Pa. in May 2014.

BRIEF SUMMARY OF THE INVENTION

The following traits represent the characteristics of the new variety 'Little Night'. These traits in combination distinguish this variety from all other commercial varieties known to the inventor.

1. Dwarf, compact habit;
2. Short, compact flowering stems (spikes) with small-sized foliage; and
3. Dark violet flowers.

Plant Breeder's Rights for this variety have not been applied for and 'Little Night' has not been offered for sale more than a year before the filing date of this application. 'Little Night' has not been promoted under any other breeder's reference or cultivar name.

Plants of 'Little Night' have not been observed under all possible environmental and cultural conditions. The phenotype may vary somewhat with variations in environmental conditions, for example, with fluctuation in temperature, soil chemistry, and photoperiod without, however, any variance in genotype.

BRIEF DESCRIPTION OF THE PHOTOGRAPH(S)

The accompanying colored photographs illustrate the overall, typical appearance of the new and distinct *salvia* plant showing the colors as true as it is reasonably possible to obtain in colored reproductions of conventional photography. Due to color variation reproduced in the photographs, color characteristics of this new variety should be determined with reference to the observations described herein, rather than a reliance on the photographs alone. Photographs were taken outdoors in May and June 2014 unless otherwise indicated. The different photographs are intended to represent the distinctive characteristics of 'Little Night'.

FIG. 1 (taken in April 2014) is a close up view of the flower spikes and leaves.

Figure 2:
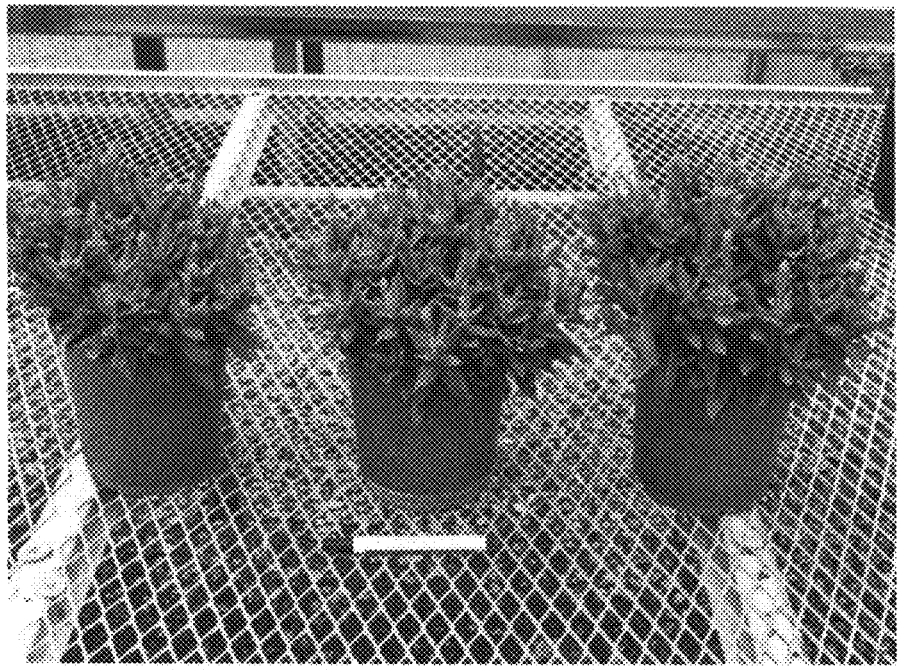

FIG. 2, taken indoors under natural light in a greenhouse setting, demonstrates the size of 18 month-old plants growing in #1 gallon pots as compared to the size of a felt-tip marker.

Figure 3:
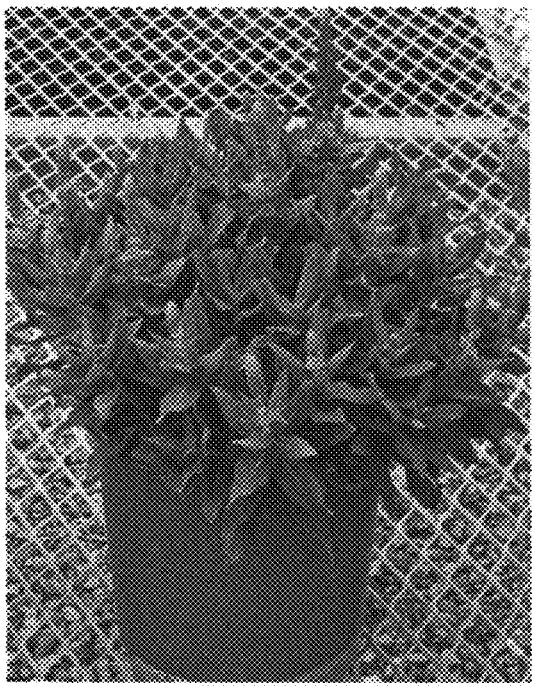

FIG. 3 is a close-up of the foliage.

Figure 4:
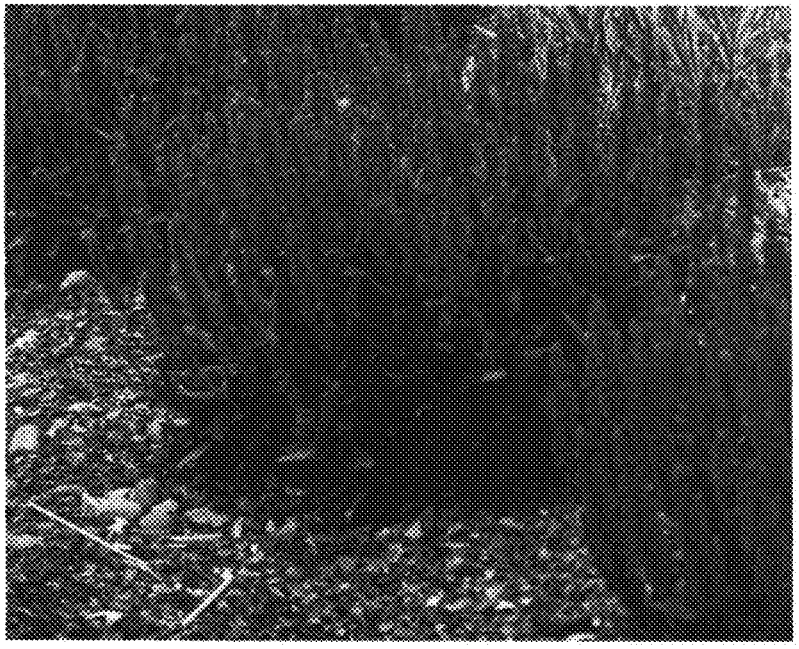

FIG. 4 demonstrates the overall habit and coloration of the invention.

DETAILED BOTANICAL DESCRIPTION

The following is a detailed description of the new variety 'Little Night'. Data was collected from a plant approximately 18 months-old in June 2014. The color determinations are in accordance with The 2007 edition of The Royal Horticultural Society Colour Chart published by The Royal Horticultural Society (London, England), except where general color terms of ordinary dictionary significance are used and color readings were observed under natural, outdoor light.

VARIETY DESCRIPTION

Classification:

- Botanical: *Salvia nemerosa* (*superba*)
- Common: European Meadow Sage

Parentage:

- Female: Unknown, likely the commercially available, *Salvia nemerosa* (*superba*) named 'May Night' (unpatented)
- Male: Unknown Propagation:

- Vegetatively

-continued

VARIETY DESCRIPTION

Plant:

- Ploidy: Diploid
- Height, unpruned (m): Short, 15.5 to 18.0 cm (stems) and 25.5 to 28.0 cm (flower spikes)
- Spread (cm): 36.0 to 46.0 cm
- Vigor: Moderate
- Growth habit: Compact, upright growing stems and flower spikes
- Life cycle duration: Perennial
- Cold tolerance: USDA zone 4
- Optimal temperature range: Very tolerant of a wide range of growing temperatures Lateral Branch:

- Quantity per plant: 8 to 12
- Strength: Strong
- Length, from point of attachment of the upper lateral branch to the top (cm): 5.0 to 20.0 cm
- Diameter (mm or cm): 2.0 mm measured from base of lateral branch
- Texture: Smooth and slightly pubescent
- Color: RHS Green 143 B
- Internode length (cm): 1.5 to 3.0 cm
- Internode color: RHS Green 143 B Leaves:

- Quantity of leaves per lateral branch, average: 12 to 20
- Arrangement: Opposite, decussate
- Size (lamina average):
  - Length (mm): 40.0 mm
  - Width (mm): Medium, 15.0 mm
- Type: Simple
- Shape: Oblong to lanceolate at top
- Apex: Rounded to acute at top
- Base: Cordate to oblique rounded
- Margin: Crenate
- Cross section: Flat
- Leaf blade length (mm): 10.0 to 30.0 mm (at top); 40.0 to 50.0 (at base)
- Leaf blade width (mm): 12.0 to 20.0 mm
- Venation: Slightly reticulate on bottom
- Surface:
  - Upper surface texture: Glabrous and slightly grooved
  - Lower surface texture: Net veined and slightly pubescent especially on veins
- Petiole:
  - Shape: Straight with slight flare at stem attachment on lower leaves, petiolate on lower leaves only and upper leaves are sessile
  - Thorns, Spines: Absent
  - Length (mm): 2.0 to 20.0 mm
  - Width (mm): 1.0 to 2.0 mm Flowers:

- Inflorescence Type: Verticillaster
- Age of plant when first bloom: 12 months
- Bloom habit (frequency in the season): Recurrent
- Time of year for first bloom: Late spring (mid-May in USDA zone 6)
- Length of blooming time (days): 4 weeks
- Color:
  - Upon opening: RHS Violet N-88A
  - Aged: RHS Purple-Violet N82-A
  - New bracts upon opening: RHS Red-Purple 72-A
  - Aged bracts: RHS Green 143B
- Structure (eg. Complete): Complete, bilabiate
- Average size:
  - Length (mm): 10.5 mm
  - Width (mm): 7.0 mm
- Arrangement: Whorled around central axis of stem
- Type: 6 per false whorl
- Fragrance: None -continued

VARIETY DESCRIPTION

Bud:

Shape: Rounded to scale-like (immature), round (mature)
Length (mm):

Immature: 2.5 mm
Mature: 5.5 mm
Width (mm):

Immature: 1.25 mm
Mature: 2.6 mm
Color, mature (before opening): RHS Green 143 B tipped with RHS Violet N88B Petal:

Number, average: 5
Arrangement: Bilabiate
Length (mm):

Posterior lip: 8.2 mm
Anterior lip: 6.8 mm
Width (mm):

Posterior lip: 1.1 mm
Anterior lip: 3.8 mm
Shape: Bilabiate: fused at bottom, zygomorphic
Apex shape: Rounded
Base shape: Fused into tube
Margin: Smooth
Pubescence: Sparsely pubescent on exterior of petal
Color: RHS Violet N88 A Throat:

Length (mm): 4.3 mm
Width (mm): 1.7 mm
Color (taken of a 3-year-old plant): RHS N87A (Violet group)

Sepals:

Number (per flower): 5
Shape: Slightly bilabiate
Length (mm): 5.5 mm
Width (mm): 2.25 mm
Apex: Lanceolate
Texture: Smooth
Color (taken of a 3-year-old plant): RHS N78A (purple group) aging to 138B (green group) with N78A streaking and tip Peduncle:

Length (mm): 12.0 to 18.0 mm
Diameter (mm): 2.0 to 2.5 mm
Angle: 180°
Texture: Stem-like, smooth with slight pubescence
Color (taken of a 3-year-old plant): RHS 147B (yellow-green group)

Pedicel:

Length (mm): 1.0 mm
Width (mm): 0.7 mm
Color (taken of a 3-year-old plant): RHS 61B (red-purple group) aging to N145C (yellow-green group)

Calyx:

Shape: United at base with lanceolate tips, slightly bilabiate
Length (mm): 5.5 mm
Diameter (mm): 1.0 mm Reproductive Organs:

Fertility, self: No

Stamen:

Number: 2
Length (mm): 1.5 mm

-continued

VARIETY DESCRIPTION

Anther:

Length (mm): 0.5 mm
Width (mm): 0.1 mm
Filament length (mm): 1.0 mm

Pistil

Number: 1
Length (mm): 11.0 mm

Style

Length (mm): 8.0 mm
Width (mm): 0.4 mm

Ovary

Shape: Round
Diameter (mm): 0.85 mm

Pollen

Amount: Minimal
Color: Yellow

Seed

Quantity: Up to 4 per flower
Shape: Round
Texture: Hard, smooth
Color: RHS 177A (greyed-orange group)
Diameter (mm): 1.3 mm Fruit Type: Schizocarp
Diameter (mm): 2.2 mm Best mode growing conditions:

*Soil conditions*.—Grows well in all types of soil conditions, including clay.

*Water use/drought tolerance*.—Drought tolerant, xeric when planted in the ground.

*Fertilization*.—None required for propagation, add standard water soluble 15-15-15 or similar formulation weekly during growing season.

Known pest susceptibility: Spider Mites.

COMPARISON TO SIMILAR VARIETIES

In comparison to the likely female parent, a commercially available, unpatented variety of *Salvia nemerosa* (superba) named 'May Night', the growth habit of the said invention, 'Little Night', is much more compact. 'Little Night' also has shorter, more compact flowering stems (spikes) and smaller foliage size.

The male parent is unknown; therefore, no comparison can be made.

'Little Night' differs from the commercially available *Salvia nemerosa* named 'Haeumanarc' (U.S. Plant Pat. No. 13,322), known commercially as Marcus, in that the flowers of 'Little Night' are a much darker violet, the flower spikes are thinner in diameter and more compact, the plant height in the flower and stem portions are shorter than 'Haeumanarc' by a few centimeters, and the parentage is different.

I claim:

1. A new and distinct *Salvia* plant as herein described and illustrated.

* * * * *